US005950262A

United States Patent [19]

Smoler et al.

[11] Patent Number: 5,950,262
[45] Date of Patent: Sep. 14, 1999

[54] ROTATABLE EXAMINATION TABLE

[75] Inventors: Martin Smoler, Mission Hills, Kans.; Michael G. Falbo, Sr., Gladstone, Mo.

[73] Assignee: American Echo, Inc., Kansas City, Mo.

[21] Appl. No.: 09/064,214

[22] Filed: Apr. 22, 1998

[51] Int. Cl.[6] .............................. A61G 7/015; A61B 5/00; A61B 19/00

[52] U.S. Cl. ............................ 5/613; 5/600; 5/937; 188/5

[58] Field of Search ................................ 5/600, 601, 613, 5/937; 188/5; 248/129; 600/300; 128/897, 898; 378/209

[56] References Cited

U.S. PATENT DOCUMENTS

| | | | |
|---|---|---|---|
| 1,040,795 | 10/1912 | Skefington | 5/613 |
| 2,845,543 | 7/1958 | Mansen et al. | 5/600 |
| 5,184,363 | 2/1993 | Falbo, Sr. | 5/601 |

OTHER PUBLICATIONS

Colson Catalog—Floor Lock Brake Part No. 9–6002–3.

*Primary Examiner*—Alexander Grosz
*Attorney, Agent, or Firm*—Hovey,Williams, Timmons & Collins

[57] ABSTRACT

A preferred patient examination table (10) includes a selectively engageable, pivot mechanism (14) allowing the table (10) to be pivoted about an upright pivot axis (98) in order to position the table (10) as needed for ready access to examination equipment (88) by performing a procedure with either a left or right hand.

14 Claims, 3 Drawing Sheets

ROTATABLE EXAMINATION TABLE

RELATED APPLICATIONS

Not applicable.

FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention relates to the field of patient examination tables. More particularly, the invention is concerned with a patient examination table including a selectively engageable, pivot mechanism allowing the table to be pivoted about an upright pivot axis in order to position the table as needed for ready usage of the examination equipment by holding a probe in either the left or right hand of an examiner.

2. Description of the Prior Art

Patient examination tables such as those for echocardiography are usually oriented with relation to examination equipment having a tethered probe in a manner that is more convenient for either left-handed or right-handed usage of the probe. When an examiner needs to examine a patient using the hand opposite of that for which the equipment was arranged, the arrangement presents an awkward and thereby inefficient situation. In the alternative, the equipment and examination table can be rearranged, but this is inconvenient and inefficient as well because the rooms are usually small and such tables are typically heavy and the equipment delicate. Moreover, the equipment is connected with a number of lines and cables that make moving of the equipment an inconvenient and a time consuming task.

SUMMARY OF THE INVENTION

The present invention solves the prior art problems mentioned above and provides a distinct advance in the state of the art. In particular, the rotatable examination table hereof enables efficient and easy rearrangement of the table for left-handed or right-handed usage of a probe for performing medical examinations.

The preferred table apparatus of the present invention includes a table assembly having a deck and a support assembly shiftably supporting the deck on a support surface such as a floor. The deck includes three access sites defined therein and the apparatus further includes a pivot mechanism for engaging the support surface at only one contact site in a manner to define an upright pivot axis for enabling rotation of the assembly about the axis.

In preferred forms, the pivot mechanism is selectively shiftable between an engaged and disengaged position. When engaged, the table can be rotated about the pivot axis as needed to accommodate left-handed or right-handed holding of a probe for performing a medical examination, for example. Other preferred aspects of the present invention are disclosed herein.

DETAILED DESCRIPTION OF THE PREFERRED EMBODIMENT

Figure 1:
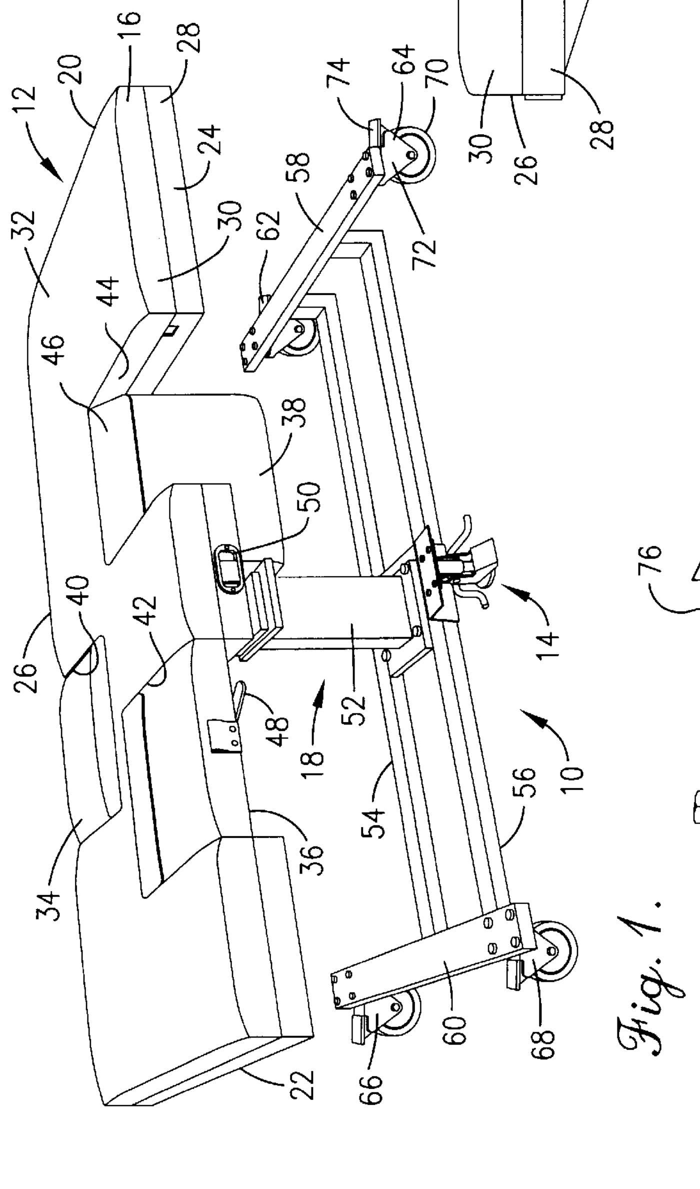
FIG. 1 is a side, top, end pictorial view of the preferred examination table in accordance with the present invention.
Figure 3:
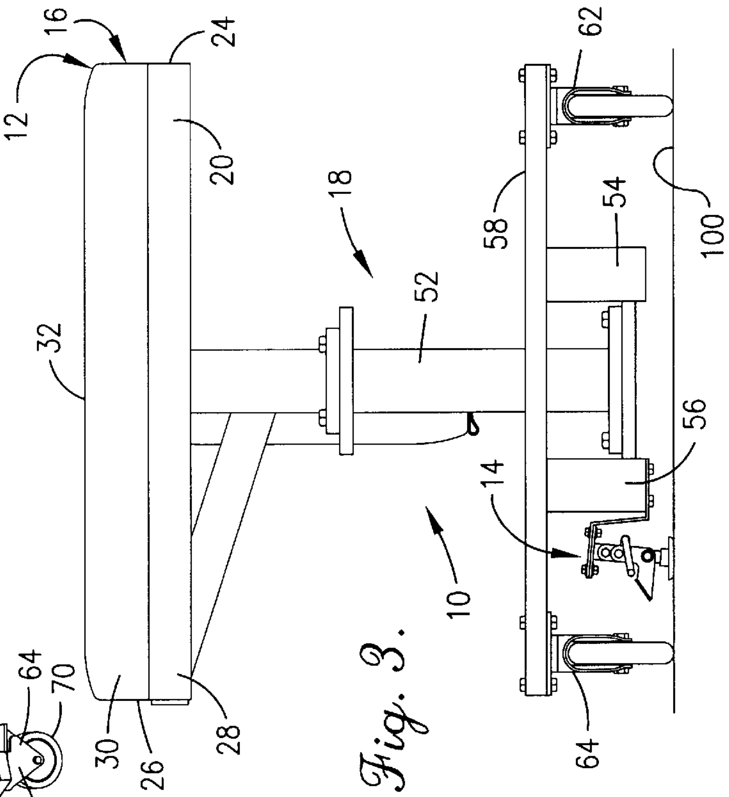
FIG. 3 is an end elevational view taken along line 3—3 of FIG. 2.

FIG. 1 illustrates preferred examination table 10 in accordance with the present invention. Table 10 broadly includes table assembly 12 and pivot mechanism 14. Table assembly 12 includes deck 16 and support assembly 18.

Deck 16 presents end 20, opposed end 22, side 24 and opposed side 26. Deck 16 further includes table frame 28 supporting cushion 30 presenting upper face 32 and first, second and third filler sections 34, 36 and 38 shiftable between closed and open positions in respective first, second and third access sites 40, 42 and 44. Deck 16 is preferably configured for supporting a patient on upper face 32 of cushion 30 in the prone position as illustrated in FIGS. 5 and 6.

Each access site 40–44 opens outwardly along a respective side of deck 16 and is preferably adjacent an inboard hinge wall 46. Each filler section 34–38 is hingedly coupled with hinge wall 46 and configured as illustrated in U.S. Pat. No. 5,184,363 hereby incorporated by reference as part of the disclosure hereof. Each section 34–38 is shiftable between an open position such as that illustrated for section 38 in FIG. 1 allowing access therethrough, and a closed position such as illustrated for sections 34, 36 in which the filler section presents a contiguous support surface with upper face 32. Additionally, each filler section 34–38 includes a conventional latch mechanism (not shown) and a release, such as latch release 48 for section 36, and remote latch release 50 for releasing section 34.

Figure 6:
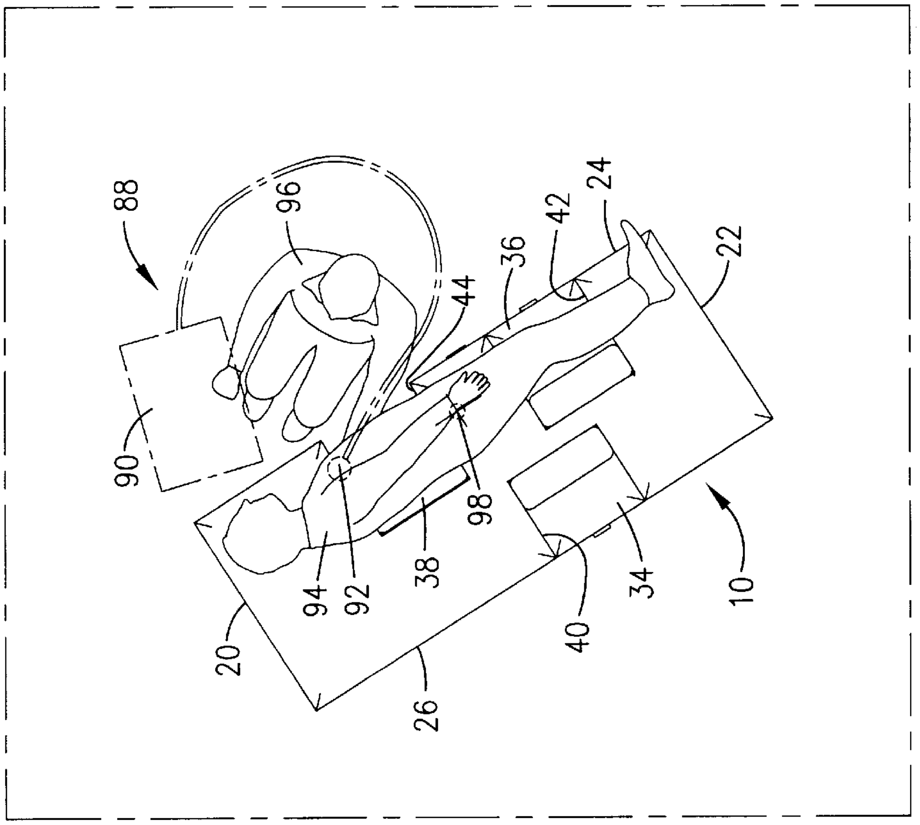
FIG. 6 is a plan view similar to FIG. 5 but showing the table rotated for use by an examiner using the left hand to hold the probe.
Figure 5:
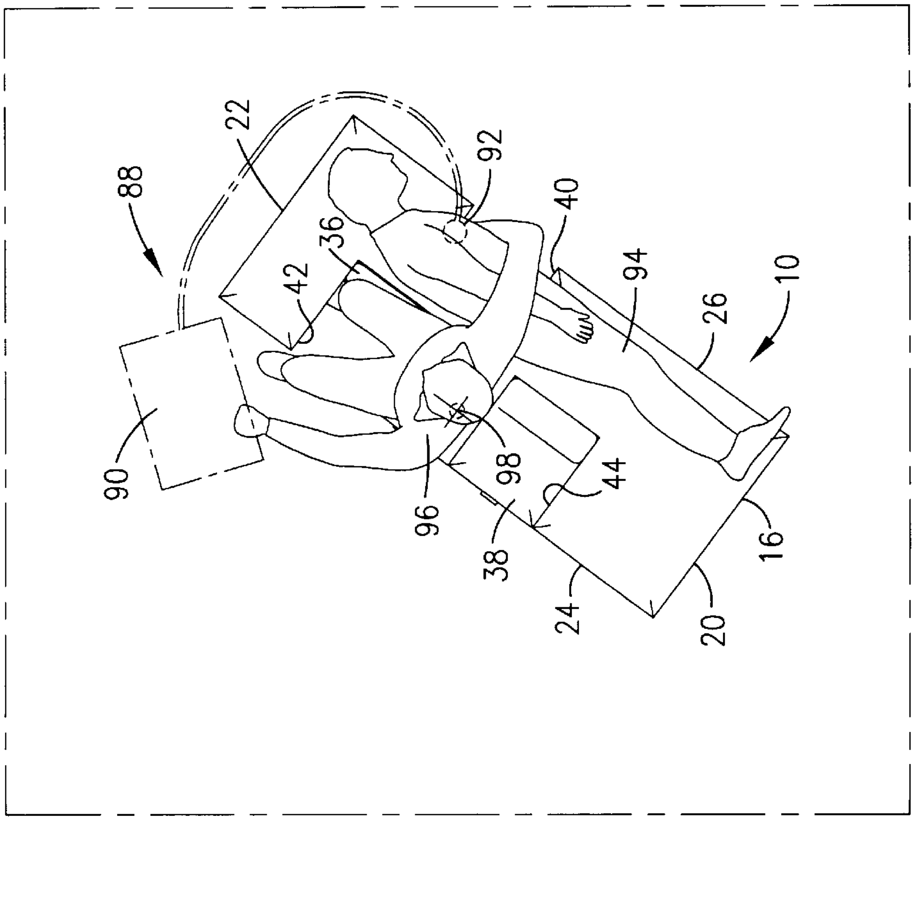
FIG. 5 is a plan view of the apparatus of FIG. 1 shown in use by an examiner using the right hand to hold the probe of an examination instrument to examine a patient lying on the apparatus.

As best viewed in FIGS. 1 and 5–6, first access site 40 is located adjacent side 26, and second and third access sites 42, 44 are located adjacent side 24 of deck 16. More particularly, first access site 40 is located adjacent side 26 of deck 16 so that a patient's heart region is positioned above site 40 when the patient is positioned as shown in FIG. 5 with the patient's head adjacent end 22. Second access site 42 is located for receiving a body portion such as the legs of a sitting examiner or torso of a standing examiner conducting a medical examination as illustrated in FIG. 5. Third access site 44 is located so that a patient's body region, such as the heart region, is positioned above site 44, allowing access therethrough for the probe of an echocardiogram instrument as illustrated in FIG. 6 with the patient's head adjacent end 20.

Conventional support assembly 18 includes pedestal 52, cross members 54 and 56, wheel arms 58 and 60 and braking casters 62, 64, 66 and 68. The upper end of upright pedestal 52 is connected to table frame 28. Spaced, parallel, cross members 54, 56 each present an upwardly site, C-shaped configuration and are connected to the lower end of pedestal 52 on opposed sides thereof and extend substantially along the length of deck 16. Wheel arms 58, 60 respectively interconnect the ends of cross members 54, 56 as best viewed in FIG. 1.

Braking casters 62–68 are conventional of the type commonly used with hospital gurneys and are coupled respectively with the ends of wheel arms 58, 60. Each braking caster 62–68 includes wheel 70, caster mount 72 and foot actuated brake arm 74. Casters 62–68 enable assembly 18 to provide shiftable, that is, rolling support of deck 16 thereby allowing linear movement in any direction, but also rotational movement about an upright axis as discussed further herein.

Figure 4:
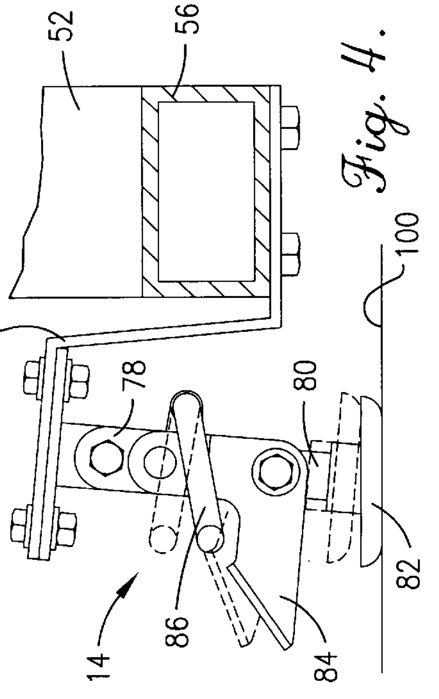
FIG. 4 is a partial sectional view taken along line 4—4 of FIG. 2.
Figure 2:
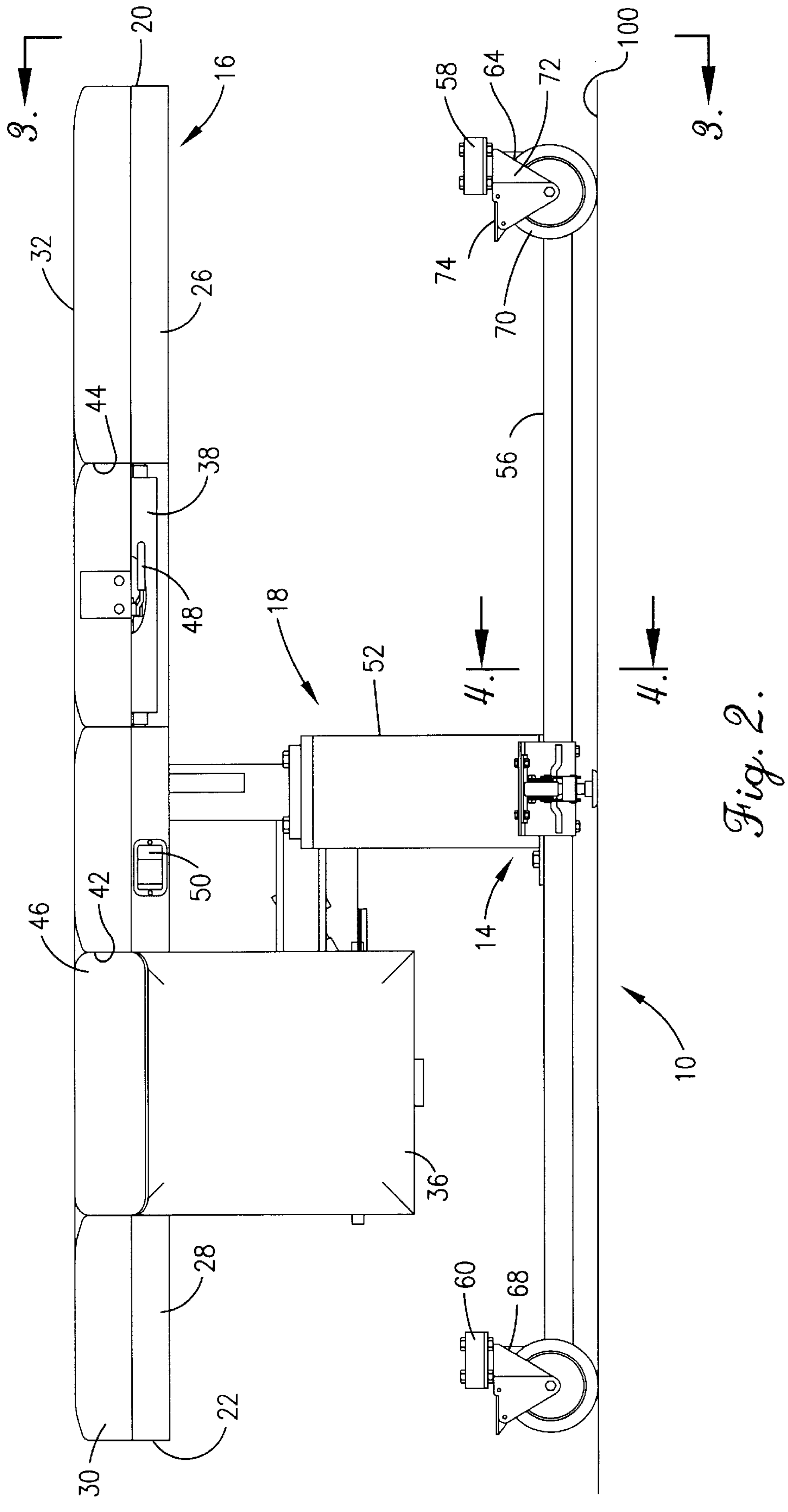
FIG. 2 is a side elevational view of the table of FIG. 1.

Pivot mechanism 14 (preferably Colson Part No. 9-6002-3 floor lock brake) includes mounting bracket 76, pivot support leg 78, pivot rod 80, pivot body 82, engagement pedal 84 and release lever 86. Pivot body 82 is preferably composed of a resilient, non-marking friction material and extends from rod 80. Pivot rod 80 and pivot body 82 are coupled with leg 78 and shiftable between a disengaged position, illustrated by the dashed lines in FIG. 4, and an engaged position, illustrated by the solid lines in FIG. 4. Pressing on, then releasing, pedal 84 causes pivot body 82 to shift to the engaged position. Pushing on release lever 86 causes body 82 to retract to the disengaged position.

FIGS. 5 and 6 illustrate one preferred environment of use for examination table 10 in order to perform a medical examination such as an echocardiogram using an examination instrument 88 having base unit 90 and probe 92 coupled with base unit 90 by a flexible tether. As shown in FIG. 5, table 10 is oriented for use by an examiner 96 holding probe 92 in the right hand for examining a patient 94. Also, the patient is in a first position over site 40 next to side 26 and with the patient's head adjacent end 22. The examiner could be a technician, physician or any other person qualified to use instrument 88.

In the orientation of FIG. 5, third filler section 38 is in the closed position relative to third access site 44. Second filler section 36 is in the open position with the legs (or torso) of the examiner 96 received in second access site 42. This allows examiner 96 to sit on deck 16 (or stand in site 42) in order to reach over and around patient 94 to position probe 92 through first access site 40 (with first filler section 34 in the open position) and into contact with the patient's heart region. As illustrated in FIG. 5, table 10 is also oriented and the examiner 96 positioned so that base unit 90 is in the range of view and within reach of the examiner's left arm for operation by examiner 96.

FIG. 6 shows table 10 in an orientation for use by the examiner 96 holding probe 92 in the left hand. As shown, table 10 has been rotated about pivot axis 98 compared to FIG. 5. To achieve this orientation, the user, such as examiner 96, presses on engagement pedal 84 which causes pivot body 82 to engage the support surface such as floor 100. Next, examiner 96 releases the brake arm 74 of each braking caster 62–68 as needed and rotates table 10 about pivot axis 98.

When pivot body 82 engages floor 100, the frictional contact therewith substantially prevents linear movement of table 10. However, such contact presents very little resistance to rotation, end for end, of table 10 about pivot axis 98. Thus, the user is able easily to rotate table 10 between the orientations of FIGS. 5 and 6 as needed. Upon achieving the desired orientation of table 10, the user then re-engages the brake arms of each breaking caster 62 and can press on release lever 86 to shift pivot body 82 to the disengaged position. It will be appreciated, however, that pivot body 82 may be left in the engaged position if desired. In this way, body 82 is already engaged for subsequent rotations of table 10.

In the orientation of FIG. 6, the patient 96 is in a second position lying adjacent side 28 over site 44 with the patient's head adjacent end 20. Also, first and second filler sections 34, 36 are closed and filler section 38 is open allowing access through site 44. The patient is positioned so that the patient's heart region is located above site 44. As shown, the examiner 96 is still positioned between table 10 and base unit 90. Moreover, base unit 90 is in the field of view and within reach of the right arm of the examiner 96. This allows examiner 96 to position probe 92, held in the examiner's left hand, through site 44 into contact with the heart region of the patient 94 without reaching over the patient 94.

As will now be appreciated, table 10 can be easily and quickly repositioned by rotation about pivot axis 98. Such is desirable where different examiners may be using base unit 90 and medical instrument 88, or where an examiner may be changing from scanning on a patient's left side to scanning on patient's right side from time to time to avoid fatigue or repetitive motion injury.

The method as described above can also be implemented without the use of pivot mechanism 14 defining axis 98. That is, casters 62–68 rollably support deck 12 and enable table 10 to be shifted as needed to the positions shown in FIGS. 5 and 6. The brakes can then be set on casters 62–68 to hold table 10 in the selected position.

Those skilled in the art will appreciate that the present invention encompasses many variations in the preferred embodiment described above. For example, other types of pivot mechanisms could be used as long as the mechanism is sufficient for defining a pivot axis. Also, the pivot mechanism can be positioned at other locations on table 10 as needed for a particular application. As another example, it is not required that the access sites open outwardly from one of the sides of deck 16. In particular, the sites could be holes through the deck, sites of different shape, or even in the configuration of contours or indentations in the side edges of deck 16. Also, it is not required that the access sites have filler sections, although such is preferred, or that the filler sections be hingedly coupled with the inboard wall of a respective site. As a final example, support assembly 18 can take on any number of configurations sufficient to support deck 16. Additionally, pedestal 52 can present a telescoping configuration, powered or manually operated, for changing the height of deck 16.

Having thus described the preferred embodiment of the present invention, the following is claimed as new and desired to be secured by Letters Patent:

1. A patient examination table apparatus comprising:

a table assembly including a deck presenting a pair of opposed ends and a pair of opposed sides, and including structure defining at least one access site adjacent one of the sides configured and positioned for receiving a body portion of an examiner to enable the examiner to examine a patient on the deck, and support means shiftably supporting said deck on a support surface; and pivot means coupled with said assembly for engaging the support surface at only one contact site in a manner to define an upright pivot axis for enabling rotation of said assembly about said pivot axis.

2. The apparatus as set forth in claim 1, said sites being located adjacent opposed sides of said deck.

3. The apparatus as set forth in claim 2, said deck including three of said sites.

4. The apparatus as set forth in claim 3, said deck including at least one filler section configured for selectively closing at least one of said sites.

5. The apparatus as set forth in claim 4, said filler section being shiftably coupled with said assembly and shiftable between a closed position in which said filler section closes said at least one of said sites, and an open position in which said at least one of said sites is open.

6. The apparatus as set forth in claim 5 further including three of said filler sections for closing said three sites respectively.

7. The apparatus as set forth in claim 1, said pivot means including means for frictionally engaging the support surface.

8. The apparatus as set forth in claim 1, said pivot means being shiftable between an engaged position and a disengaged position.

9. The apparatus as set forth in claim 1, said pivot means including a pivot body composed of resilient material and a shifting mechanism for placing said pivot body in snug engagement with support surface for enabling said rotation.

10. The apparatus as set forth in claim 1, said pivot means further including a foot lever for selectively activating said shifting mechanism for shifting said pivot body between engaged and disengaged positions relative to the support surface.

11. The apparatus as set forth in claim 1, said support means including a plurality of casters.

12. A patient examination table apparatus comprising:

a deck; and support means shiftably supporting said deck on a support surface, said deck presenting a first end and an opposed second end, and a first side and an opposed second side, and including structure defining a first access site adjacent said first side and second and third access sites adjacent said second side, said first site being configured and positioned for receiving a medical examination probe therethrough from below said deck into contact with the heart region of a patient lying on said deck in a first position with the patient's head adjacent said first end, said second site being configured and positioned for receiving a body portion of an examiner to enable the examiner to reach over a patient in said first position and place the probe held in the examiner's right hand into contact with the patient's heart region through said first site, and said third site being configured and positioned for receiving a medical examination probe therethrough from below said deck into contact with the heart region of a patient lying on said deck in a second position with the patient's head adjacent said second end.

13. The apparatus as set forth in claim 3, said support means including a plurality of braking casters.

14. The apparatus as set forth in claim 6, further including three filler sections configured for selectively closing said sites respectively.

* * * * *